(12) United States Patent
Larm et al.

(10) Patent No.: US 6,630,458 B2
(45) Date of Patent: Oct. 7, 2003

(54) TEAT DIPPING AGENT

(75) Inventors: Olle Larm, Bromma (SE); Marcus Back, Vällingby (SE)

(73) Assignee: Medicarb AB, Bromma (SE)

( * ) Notice: Subject to any disclaimer, the term of this patent is extended or adjusted under 35 U.S.C. 154(b) by 0 days.

(21) Appl. No.: 09/202,930

(22) PCT Filed: Apr. 28, 1998

(86) PCT No.: PCT/SE98/00776
§ 371 (c)(1),
(2), (4) Date: Jan. 19, 1999

(87) PCT Pub. No.: WO98/48627
PCT Pub. Date: Nov. 5, 1998

(65) Prior Publication Data
US 2002/0103159 A1 Aug. 1, 2002

(30) Foreign Application Priority Data
Apr. 29, 1997 (SE) .............................................. 9701616

(51) Int. Cl.⁷ .................... A61K 31/722; A61K 31/721; A61K 31/727; A61K 47/10; A61K 47/38
(52) U.S. Cl. ......................... 514/55; 424/405; 514/54; 514/56; 514/59; 514/772; 514/781
(58) Field of Search ............... 514/54, 55, 56, 514/59, 772, 781; 424/405

(56) References Cited

U.S. PATENT DOCUMENTS 5,100,879 A * 3/1992 Ueno et al. .................... 514/59

FOREIGN PATENT DOCUMENTS

| JP | 06024934 A | 2/1994 |
|---|---|---|
| RU | 2048473 | 11/1995 |
| WO | WO94/16714 | 8/1994 |
| WO | WO95/30403 | 11/1995 |
| WO | WO96/02260 | 2/1996 |
| WO | WO 98/05341 A1 | 2/1998 |

OTHER PUBLICATIONS

Post et al. Association of caprine arthritis encephalitis virus (CAEV) with mastitis in goats. Bulletin of the Intenational Dairy Federation, No. 202, pp. 902–907 (1986).*
STN/CAS online, file CANCERLIT, Acc. No. 89045582 (Cutlip et al.. Ovine progressive pneumonia (maedi–visna) in sheep. Veterinary Microbiology, vol. 17, No. 3, pp. 237–250 (1988)), Abstract.*
STN/CAS online, file SCISEARCH, Acc. No. 96:395416 (Kirk et al.. Mastitis in ewes. Compendium On Continuing Education For The Practicing Veterinarian, vol. 18, No. 5, pp. 582–590 (1996).*
Takenaka et al., JP 04169529, Livestock mastitis–preventing agent and preparation thereof (1992), West Online, file JPAB, abstract.*
International Search Report (Form PCT/ISA 210) for PCT/SE02/00318, Completed by the Swedish Patent Office, Mailed Jun. 13, 2002.

* cited by examiner

Primary Examiner—Jose' G. Dees
Assistant Examiner—Frank Choi
(74) Attorney, Agent, or Firm—Burns, Doane, Swecker & Mathis, L.L.P.

(57) ABSTRACT

Use of a composition comprising chitosan in combination with a polysaccharide selected from heparin, heparan sulphate and dextran sulphate, as an active component in a solvent, for the manufacture of a teat dipping solution for lactating animals, particularly cows. The invention also relates to a process for prophylactic or wound healing treatment of lactating animals, particularly cows, against mastitis.

21 Claims, 3 Drawing Sheets

Control= Untreated agar plate

Chitosan-dextran sulphate=1.0% chitosan + 0.02% dextran sulphate + 0.1% methyl cellulose + 0.5% glycerol.

Iodine=Commercial dipping agent containing iodine
Streptococcus= Strept.agalactiae, Strept. dysgalactiae, Strept. uberis Control= Untreated agar plate Chitosan-dextran sulphate=1.0% chitosan + 0.02% dextran sulphate + 0.1% methyl cellulose + 0.5% glycerol.

Iodine=Commercial dipping agent containing iodine
Streptococcus= Strept.agalactiae, Strept. dysgalactiae, Strept. uberis Infection frequency of untreated, chitosan-dextran sulphate treated and iodine treated udder parts.

ns. A large number of different bacteria have been identified as mastitis pathogens. They have been divided into four different groups, contagious, environmental, opportunistic and other bacteria. The majority of the mastitis infections are caused by *S. aureus*. Another contagious mastitis pathogen is *Streptococcus agalactiae*. Among the environmental bacteria there are other streptococci and the coliform bacteria, such as *Escherichia coli* and *Klebsielle pneumoniae*.

TEAT DIPPING AGENT

TECHNICAL AREA

The present invention relates to the area teat dipping agents for lactating animals. More in particular it relates to a teat dipping agent based on components which are new within this technical area. This new teat dipping agent possesses several advantages in relation to known teat dipping agents.

BACKGROUND OF THE INVENTION

Mastitis is an inflammatory reaction of udder tissue and is the most common and most costly disease among lactating cows over the world. The inflammation is a reaction of the lactating tissues on the presence of infectious microorganisms. A large number of different bacteria have been identified as mastitis pathogens. They have been divided into four different groups, contagious, environmental, opportunistic and other bacteria. The majority of the mastitis infections are caused by *S. aureus*. Another contagious mastitis pathogen is *Streptococcus agalactiae*. Among the environmental bacteria there are other streptococci and the coliform bacteria, such as *Escherichia coli* and *Klebsielle pneumoniae*.

A large number of different disinfectants (most frequently chlorohexidine or iodophors) are used for dipping the teats immediately after milking in order to prevent bacteria from penetrating into the teat canal and further to lactating tissues. These disinfectants have a killing effect in direct contact between disinfectant and bacterium. In spite of routine use of these agents a number of bacteria escaped the killing effect, i.e. the known agents are not sufficiently effective, which can be due to insufficient amount of active components and the fact that the agents do not reach sufficient contact with the infected sites. It is also known that the effect of these agents fades out very quickly and that renewed contamination of the teats takes place shortly after the treatment. Small wounds and skin tissues on the teats can act as reservoirs for certain bacteria, and live stock with infected teat wounds often show higher mastitis frequencies than other live stock. Furthermore, iodine and chlorohexidin can result in taste changes of the milk and relatively small quantities of iodine and chlorohexidin in milk can cause problems in the manufacture of dairy products.

DESCRIPTION OF THE INVENTION

The present invention thus relates to a new teat dipping composition for lactating animals, which composition represents a substantial contribution to the technology within the area since it has been found to show improvement in several respects compared to existing teat dipping compositions.

More in particular, it has, in accordance with the invention, surprisingly been found that a combination of chitosan and a group of polysaccharides functions quite well as active components in such teat dipping composition. Several different effects and advantages have been observed. Quite generally, it means that the composition according to the invention shows higher activity than known teat dipping agents of the type chlorohexidin and iodophors. An effect in this context is that the new teat dipping composition forms a long time barrier at the teat canal opening and prevents bacteria from penetrating into the teat canal. Furthermore, the composition has a growth inhibiting effect on bacteria and a healing effect on skin wounds further strengthening the protection. This means that the composition can be used for a pure bacteria barrier or bacteriostatic effect, by which follows that it can be used as a prophylactic agent against mastitis. In addition, the composition assists in the healing of wounds and skin fissures. Furthermore, the composition can be given such consistency that it is easy to apply to the teats, for example by dipping or spraying, at the same time as it imparts a softening effect on the teats.

It can be added in this context with regard to prior art that a composition similar in composition is know per se from for example WO96/02260. However, this known composition has not been referred to or remotely indicated as a teat dipping composition, much less is there in the prior art any indication about the fact that it in such context even shows higher activity than known teat dipping agents of the type chlorohexidin and iodophors.

The expression teat dipping in connection with the present invention shall be interpreted broadly and in accordance with the terminology used within this technical area. Thus, the composition is not only intended for a dipping of the teats in same but it can, of course, also be applied in another way, such as by spraying, but still fall within the recognised term teat dipping composition or agent.

A first object of the invention is, with other words, to provide a teat dipping composition intended to be used for its bacteria barrier effect or bacteriostatic effect.

Another object of the invention is to provide a composition which, when applied, results in a wound healing effect.

Yet an object of the invention is to provide a composition which, when applied, results in a prophylactic action against mastitis.

Another object of the invention is to provide a composition, which has such consistency that it is extremely well suited for dipping or spray application on the teats of lactating animals, at the same time as it thereby imparts a softening effect.

A further object of the invention is to provide a composition which assists in a faster and qualitatively improved healing of wounds on the teats.

Other objects and advantages of the invention will be clear from the more detailed description thereof below.

DETAILED DESCRIPTION OF THE INVENTION

Figure 1:
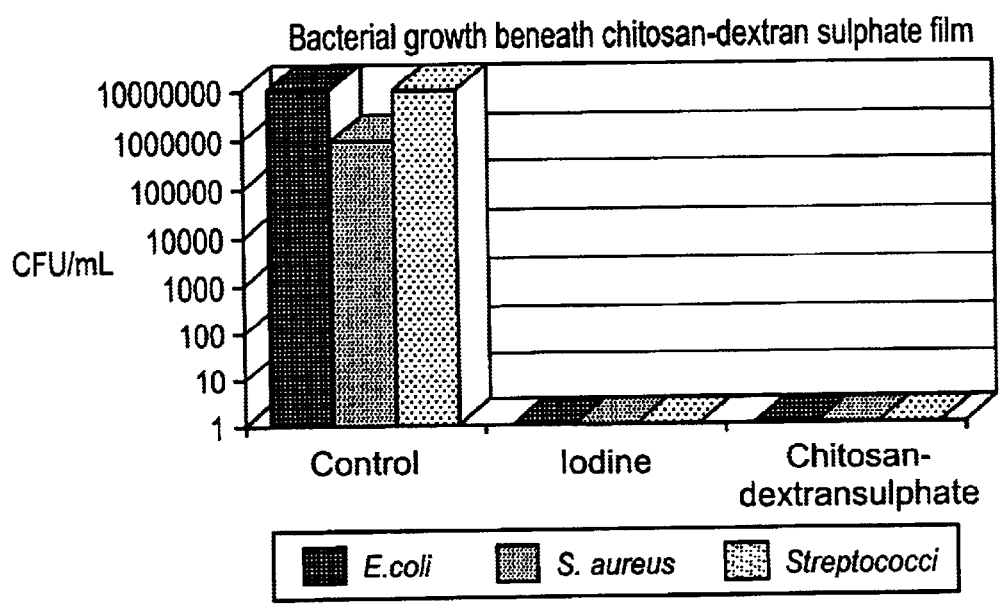
FIG. 1 shows bacterial growth beneath a chitosan-dextran sulphate film. Specifically, the bar graph shows bacterial growth beneath a chitosan-dextran sulphate film, wherein the bacteria (*E. coli, S. aureus* or Streptococci) are treated with iodine or chitosan-dextran sulphate.

More in particular, the invention relates to use of a composition comprising chitosan in combination with a polysaccharide selected from heparin, heparan sulphate and dextran sulphate, as an active component in a solvent, for the manufacture of a teat dipping solution for lactating animals, particularly cows.

The composition according to the invention is useful for all kinds of lactating animals but, of course, in the first place cows. It is further presented in the form of a solution of the active component in a solvent, said solution with regard to consistency or viscosity generally being adapted to the method of application in a conventional manner.

From the above it is clear that the invention primarily is based on the specific combination of chitosan and the indicated polysaccharide and that primarily it is not restricted to any specific ratio between said components. The ratio between the components and the total quantity of same in the solution are therefore, in other words, to be determined by the expert in each individual case depending on the effect desired.

However, in accordance with the invention it is primarily a question of using the stated components in such quantities that the solution when applied results in a bacteria barrier effect or bacteriostatic effect.

Yet another embodiment means that the composition comprises chitosan and the stated polysaccharide in such quantities that the solution when applied results in prophylactic effect against mastitis.

Although the invention is not restricted to any specific total concentration of the active components it is generally suitable that the total concentration of chitosan plus polysaccharide in the solution is within the range 0.2–10, particularly 0.2–5, for example 0.25–3 percent by weight, based on the total weight of the solution, where the upper limit is mainly dictated by economic factors.

According to a preferred embodiment of the invention the weight ratio chitosan:polysaccharide in the composition according to the invention lies within the range 100:1–10:1, particularly 60:1–15:1.

With regard to the component chitosan it is constituted by a polysaccharide consisting of 1.4-β-bound D-glucose amine units. Said polysaccharide is linear and the properties can vary according to the degree of N-acetylation. In the nature all amino groups are acetylated and the polysaccharide is then called chitin corresponding to the shell of inter alia insects and shellfish. Chitosan is manufactured by N-deacetylation of chitin. Commercially, chitosan is recovered from crab and shrimpshells which are waste products from the fishing industry. When treating chitin with alkali, usually sodium hydroxide, N-deacetylation takes place, i.e. acetamido groups are converted into amino groups. By controlling the conditions for this alkali treatment chitosans of varying degree of N-acetylation can be manufactured.

In connection with the invention said chitosan, according to a preferred embodiment, has an N-acetylation degree of at most about 90%. In particular, said N-acetylation degree is at most about 50%, in some cases at most about 25%.

Accordingly, the polysaccharide used in the teat dipping composition according to the invention is selected from heparin, heparansulphate and dextransulphate, and these are commercially available on the market from several manufacturers. Within the framework of the invention are, furthermore, partially hydrolysed forms of these polysaccharides as long as they essentially maintain the activity desired in the context. The expression polysaccharide shall, in other words, be interpreted broadly in connection with the invention. The particularly preferred polysaccharide is, however, dextransulphate since it shows very good activity at the same time as it is considerably cheaper than the other polysaccharides.

As a carrier or matrix the composition according to the invention contains a conventional one, usually an aqueous carrier, for example pure water.

The solution is imparted suitable consistency or viscosity suitable for the application method used and this can be obtained according to conventional technology. As exemples of viscosity controlling agents for use in the composition according to the invention, there may be mentioned hemicellulose types, for example arabinoxylanes and glucomannanes; plant gum materials, for example guar gum and johannistree gums; cellulose types and derivatives thereof, for-example methyl cellulose, ethyl cellulose, hydroxyethyl cellulose or carboxymethyl cellulose; starch and starch derivatives, for example hydroxyethyl starch or crosslinked starch; microbial polysaccharides, for example xantan rubber, curdlan, pullulan or dextran; and glycerol. Particularly preferred viscosity controlling agents are, however, different types of cellulose and derivatives thereof, particularly methyl cellulose, and glycerol.

Since the composition described above can be used as a barrier-forming teat dipping agent for lactating animals without any therapeutic effect another aspect of the invention relates to the use of the composition as defined above as a barrier-forming or bacteriostatic teat dipping agent for lactating animals, particularly cows.

Since the composition, furthermore, can be utilised to counteract mastitis according to another aspect of the invention it represents the use of said composition for the manufacture of a teat dipping agent having prophylactic action against mastitis of lactating animals, particularly cows.

A further aspect of the invention is represented by a method for prophylactic treatment of lactating animals, particularly cows, against mastitis, where on the teats of said animals a composition according to the above definition in a quantity effective for preventing the generation of mastitis is applied.

The composition according to the invention can be prepared by dissolving the active components and, optionally, additives, such as for example viscosity controlling agents, in the selected solvent in the desired concentration. An advantageous method in connection with the composition according to the invention resides in dissolving chitosan and polysaccharide separately in a suitable quantity of solvent, for example about half each of the quantity solvent totally used. The additives, for example the viscosity controlling agents, are thereby dissolved together with the polysaccharide before both solutions of chitosan and polysaccharide are admixed to a common solution which is carefully admixed, for example in a mixer, to a final teat dipping solution.

EXAMPLES

The invention will now be further illustrated by the following non-limiting examples.

Example 1

General Procedure

Vertical agar plates are covered with chitosan-dextransulphate solution before they are dipped in concentrated bacteria solutions and after said dipping. Chitosan-dextransulphate is compared with commercial iodine solution used as a teat dipping agent, and the agar plates are treated in exactly the same manner with iodine solution. The agar plates are incubated in a heating cabinet over night and the number of bacteria colonies are calculated and recorded as cfu/mL of the bacteria solution. Controls are untreated agar plates.

Materials and Reagents

E-coli, isolated from mastitis infection (Mastitlaboratoriet, SVA) S.aureus, isolated from mastitis infection (Mastitlaboratoriet, SVA) Strept. agalactiae, Strept. dysgalactiae and Strept. uberis, isolated from mastitis infection (Mastitlaboratoriet, SVA) Soy broth, Tryptic soy broth, Difco 0370-01-1 Verical agar plates, Uricult Orion UF009

Sterile bench, Kojair, LAF 7022 Photometer, Shimadzu UV-1201 Shake incubator, Orbit Environ-Shaker, Lab-Line In struments Inc. Heat cabinet, Memmert NaCl, Riedel-de Haën 31434 Chitosan, Seacure 343, Pronova Biopolymer Acetic acid, Riedel-de Haën NaOH Methyl cellulose, Sigma M-0387 Glycerol, Johnson Mat-they Electronics 13797 Dextran sulphate, Pharmacia iodine solution, Dipal, Alfa Laval 997515-80

Procedure

*E.coli* and *S.aureus* and three different streptococci (*Strept. agalactiae, Strept. dysgalactiae* and *Strept. uberis*) are sterile transferred (sterile bench) with loop from storage agar to separate sterilized trypton soy broth and incubated over night at 37° C. in a shake incubator. The following morning the bacteria are washed three times with a physiological salt solution. The optical density at 650 nm was measured with a photometer, and by means of standard curves the bacteria density was adjusted.

Chitosan-Dextran Sulphate Solution 1 g chitosan was dissolved in 50 mL sterile water, and the pH was adjusted to 5.8. 0.5 g glycerol and 0.1 g methylcellulose and 0.02 g dextransulphate were dissolved in 50 mL sterile water. Equal amounts of chitosan solution and glycerol+methyl cellulose+detransulphate solution were mixed in a mixer.

Iodine Solution

The base solution was diluted according to the instruction 6 times with water for giving a solution for use.

Bacteria Tests (i) Bacterial growth under chitosan-dextran sulphate film.

Each bacterial type was treated separately according to the following:

Three agar plates were lowered into the bacteria solution, and two of the agar plates were then dipped three times in each of the above solutions. One agar plate was left untreated.

(ii) Bacteria growth on top of chitosan-dextran sulphate film.

Each type of bacterium was treated separately according to the following:

Two agar plates were dipped three times in each of the above solutions. One agar plate was left untreated. All three agar plates were then immediately quenched in the bacteria solution.

The agar plates were incubated over night in a heat cabinet at 37° C. Then the plates and the number of colonies were inspected and registered.

Results

TABLE 1

Bacterial growth under chitosan-dextran sulphate film

| Patogene | Control | CFU/mL Chitosan-dextran sulphate | Iodine |
|---|---|---|---|
| E. coli | 10 000 000 | 0 | 0 |
| S. aureus | 1 000 000 | 0 | 0 |
| Streptococci | 10 000 000 | 0 | 0 |

TABLE 2

Bacterial growth on top of chitosan-dextran sulphate film

| Patogen | Controll | CFU/mL Chitosan dextran sulphate | Iodine |
|---|---|---|---|
| E. coli | 10 000 000 | 0 | 10 000 000 |
| S. aureus | 1 000 000 | 0 | 1 000 000 |
| Streptococci | 10 0000 000 | 0 | 10 000 000 |

Figure 2:
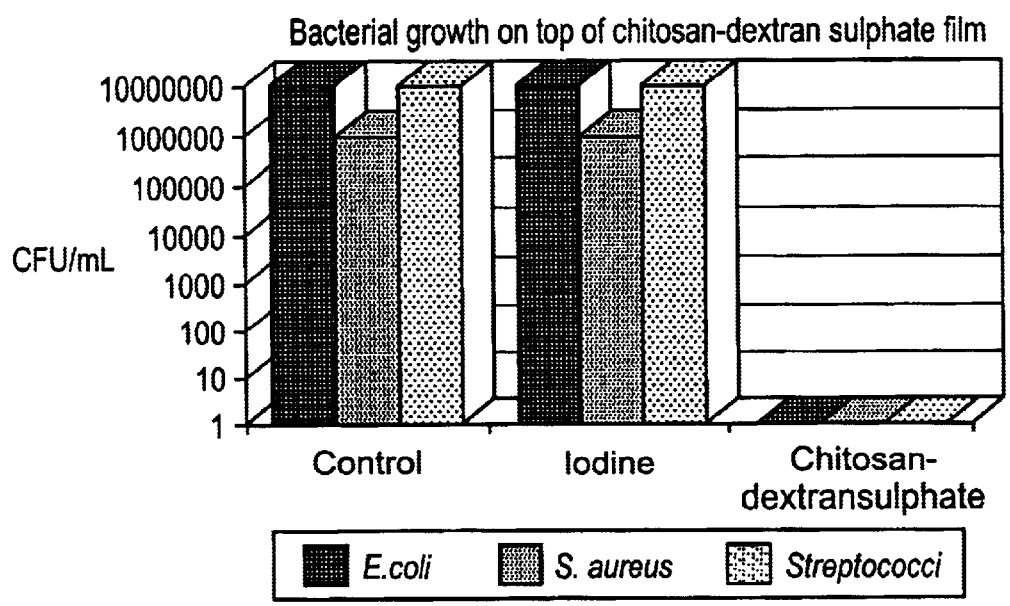
FIG. 2 shows bacterial growth on top of a chitosan-dextran sulphate film. Specifically, the bar graph shows bacterial growth on top of a chitosan-dextran sulphate film, wherein the bacteria (*E. coli, S. aureus* or Streptococci) are treated with iodine or chitosan-dextran sulphate.

The results are presented in FIGS. 1 and 2.

Example 2

Materials and Methods 6 cows of an age of 3–5 years were involved in the study. Five of the cows were of SRB-rase (Svensk Rödbrokig Boskap) and the sixth was a crossing between the SRB and SLB (Svensk Låglands Boskap). The animals were acquired from one and the same stock and were bought 12 days before initiating the experiments. The cows were stabled and a maintenance ration of fodder was composed similar to the maintenance ration of fodder that the cows had had in their original stock. The maintenance ration of fodder consisted of hay, grass ensilage, rich food and concentrate. The cows were collared in long stalls with rubber mat and cutter shavings as a litter bed.

Five cows were in the first lactation and one cow was in its third lactation. The stage of lactation varied between the second to the seventh lactation month. The yield of milk in the start of the experiments varied between 28–48 kgs ECM. The udder health was documented to be good before the start of the experiments, with negative cultivation tests and CMT-values of 1 and 2. However, coagulase negative staphylococci grew in one udder section (forward left) on one cow, together with increased cell contents (CMT 3), in view of which this udder section was excluded from the experiment.

A teat dipping solution containing (percent by weight) 1% chitosan, 0.02 dextran sulphate, 0.1% methyl cellulose and 0.5% glycerol was prepared.

Milking was carried out at $07^{30}$ and at $15^{30}$. Milk samples were taken directly after each milking situation for bacterial growth and analysis of the cell contents.

The cell contents were determined with a fluorooptoelectronic method (Fossomatic 90, A/S N. Foss Electric Denmark). The bacteriological analysis was carried out by smearing 10 $\mu$l of the milk sample on to a bovine blood agar plate with esculine added and was incubated at 3–7° C. for two days. Recordings were made after 24 and 48 hours and any mastitis pathogenic bacteria were isolated and identified. In connection with bacterial growth also routine CMT-analysis was made (California Mastit Test)

The study was carried out in three experimental rounds. In the first experimental round the animals were divided up so that three cows with together 12 udder sections were teat-dipped diagonally right forward and left rear, and three cows were teat-dipped reversed diagonally, i.e. left forward and right rear (see Table 5). The other 11 udder sections were left untreated as controls.

To the second experimental round four of the cows having 10 udder sections not infected in the first experiment were used. The udder sections were randomly distributed so that five were treated with the new teat dipping agent and five constituted controls. Two cows contributed with 3 udder sections each and two udder sections each and the two others with two udder sections each, see Table 5.

For the third experimental round four of the cows were used with seven udder sections which had not become infected during the previous experimental rounds. All 7 udder sections were treated with commercial teat dipping agent containing iodine. Two cows contributed with one udder section each and the two others with 2 and 3 udder sections, respectively, each, see Table 8.

In order to make the udder sections more sensitive to infection during the experiment keratin was removed from the teat canal on all udder sections. This was done with a darning-needle (John James & Sons, Ltd, Studley, Warwickshire, size 16). Keratin was removed from all teat canals after each morning milking.

In the first experimental round the keratin removal was terminated day 8. For two cows which up to day 7 had not become infected keratin removal was carried out both morning and night day 7 and 8.

In the second experimental round the keratin removal was terminated day 6, here double keratin removals did not have to be performed in order to infect the cows.

In the third experimental round the keratin removal was terminated day 8. Keratin removal was carried out both morning and night day 7 and 8.

Ten minutes after the teat dipping procedure all teats were dipped for 10 seconds in a bacteria suspension, containing about $1-7 \times 10^7$ CFU/ml of a β-hemolysing *Streptococcus agalactiae* strain (S-B8).

The criterium for infection of an udder section was two subsequent milk samples having bacterial growth or increased cell contents. A cow with symptom for acute clinical mastitis was treated with antibiotic and increased milking frequency.

Experimental Schedule

Morning Milking

1. After milking the teats were cleaned with 70% ethanol. The ethanol was allowed to evaporate and milk samples were then taken in test tubes from each udder quarter.

2. The teats were then carefully washed with 70% ethanol. A sterile darning-needle was inserted into the teat canal, rotated and then withdrawn. All teats were treated in this manner.

3. The pre-determined teats were immediately after point 2 dipped with teat dipping agent. The control teats were left untreated.

4. After 10 minutes all teats were dipped for 10 seconds in the bacterium suspension with $1-7 \times 107$ CFU/ml of 8-hemolysing Streptococcus agalactiae.

Night Milking

1. After milking the teats were cleaned with 70% ethanol. The ethanol was allowed to evaporate and milk samples were then taken in test tubes from each udder quarter.

2. The predetermined teats were dipped immediately after point 1 with teat dipping agent. The control teats were left untreated.

3. After 10 minutes all teats were dipped in bacterium suspension for 10 seconds.

Statistic evaluation has been made by means of $\chi^2$-analysis according to the following formula.

$$\sum \frac{(O-E)^2}{E}$$

and 95% confidence interval was calculated by means of the formula $$(p_1-p_2) \pm 1,96 \times se(p_1-p_2)$$

wherein $se(p_1-p_2)$ has been calculated as $$\sqrt{\frac{p_1(1-p_1)}{n_1} + \frac{p_2(1-p_2)}{n_2}}$$

se=standard error $n_1$=number of infected non-treated udder sections $n_2$=number of infected treated udder sections $p_1$=number of non-treated udder sections/$n_1$ $p_2$=number of treated udder sections/$n_2$ Results In total 14 of the 33 udder sections were infected during the two experimental rounds, of these were 12 not teat dipped and two were teat dipped. All cows in experimental rounds 1 and 2 became infected. In experimental round 3 two of the cows became infected.

The number of days between start of experiments and up to infection of udder sections varied between 2 and 9 days.

TABLE 3

The number of infected udder sections after treatment with teat dipping agent compared with no teat dipping (control). Experimental rounds 1 and 2 are assembled to one table.

|  | Treated | Control | Total |
|---|---|---|---|
| Infected | 2 | 12 | 14 |
| Not infected | 14 | 5 | 19 |
| Total | 16 | 17 | 33 |

TABLE 4

The number of infected udder sections after treatment with commercial teat dipping agent. Experimental round 3.

|  | Treated |
|---|---|
| Infected | 2 |
| Not infec | 5 |
| Total | 7 |

Experimental Round 1

Of the control udder sections 7/12 were infected and of teat dipped udder sections 1/11 were infected.

Five cows were infected with *Streptococcus agalactiae* in one udder section, the udder sections infected were controls.

One cow (No. 335) was infected in 3 udder sections, 2 control udder sections and 1 teat dipped udder section. The udder section of cow 335 which was strongly infected and reacted with the highest cell contents in the milk was one control section, see tables 5 and 6.

Experimental Round 2

Out of the control udder sections 5/5 were infected and out of teat dipped udder sections 1/5 were infected, see table 7.

Cow 334 was infected in all 3 udder sections part-taking in the experiment, 2 udder sections were controls and 1 udder section was treated. It was the treated udder section that became most infected and responded with a strong inflammatory reaction in the form of swelling, soreness and increased cell contents.

The other three cows in the experiment were infected in one control udder section each, see table 7.

Experimental Round 3

Out of the 7 udder sections treated with commercial iodine teat dipping agent, 2 udder sections were infected, see Table 8.

The result of the $\chi^2$-analysis for the assembled experimental results from rounds 1 and 2 gave an $\chi^2$-value of 11.39, which corresponds to a probability value of <0.1% at one degree of liberty. I.e., the probability to obtain such a deviating value as 11.39, if $h_o$ (the zero hypothesis) starts from the assumption that there is no difference between treated and untreated group, is less than 0.1%.

When calculating 95% confidence interval for the difference in proportion ($p_1 \times p_2$) between the two experimental groups the result was $0.581 \pm 1.96 \times 0.138$, i.e. between 0.311 and 0.851.

Only 7 udder sections were part of experimental round 3. These were constituted by udder sections resisting infection for the longest period of time and were therefore the result of a selection. In view of this no statistic evaluation of this experimental round was made.

Figure 3:
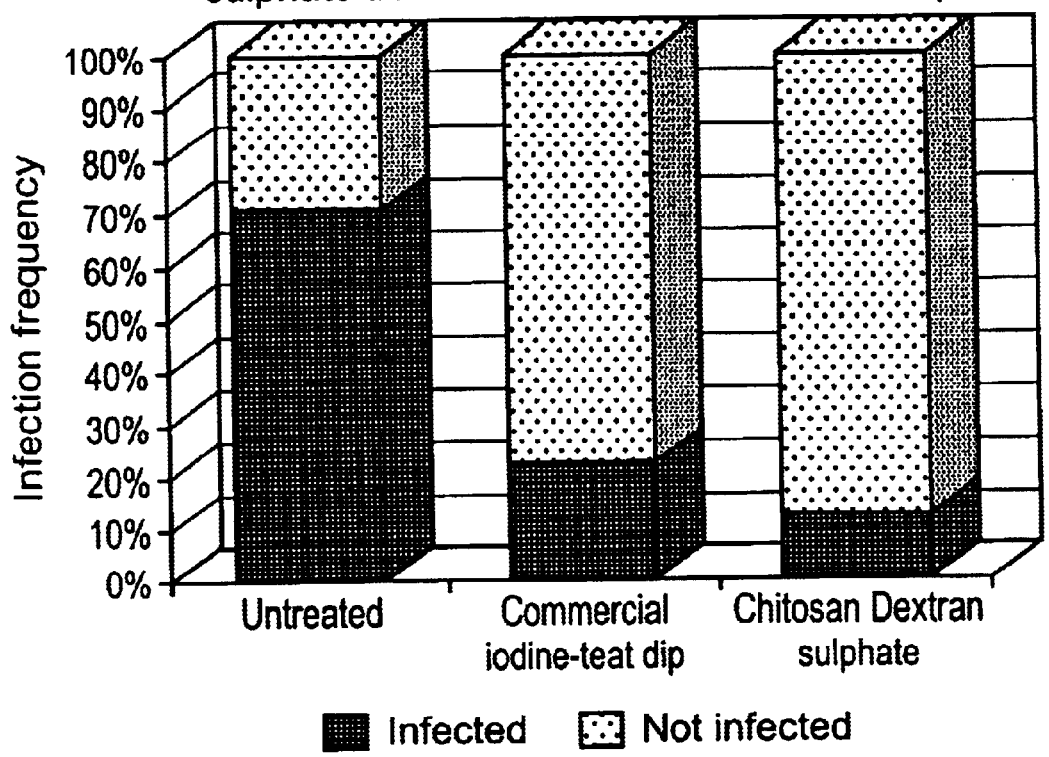
FIG. 3 shows the infection frequency of untreated, chitosan-dextran sulphate treated and iodine treated udder parts. Specifically, the bar graph illustrates infection frequency of untreated, chitosan-dextran sulphate treated and iodine treated udder parts by showing percentage infected versus not infected.

The infection frequency of the different experimental rounds is summarized in FIG. 3.

Discussion

All cows originated from the same live stock and had thereby the same immunological background. This was an advantage since one could expect that the cows would react in essentially the same manner during the readjustment period to the new environment including new maintenance ration of fodder. This resulted, together with the maintenance ration of fodder that was similar to that the cows were used to, in a situation whereby the time for buying the cows to the start of the experiments could be kept short (by 10 days).

*Streptococcus agalactiae* was selected in order that the animals with high probability would not have been subjected to this bacterium earlier, it is easy to find in cultivation (β-hemolysing), it is strictly udder specific and it is documented sensitive to penicillin.

The cows which were infected in 1 udder section in experimental rounds 1 and 2 became so in the untreated udder section, whereas the cows receiving infection in teat dipped udder sections became simultaneously infected in untreated udder sections.

In order to increase the infection risk of two cows which in the first experimental round were not infected up to day 7, the removal of keratin was extended to two times a day. The rate of generation of teat canal keratin is high (12–36 h) and probably varies between individuals in view of which they have different sensibility for similar challenges in this context. Also the quantity of keratin, the majority of the keratin and composition thereof can vary between individuals.

It can be noted that animals infected late in the first experiment were also infected late in the second experiment.

TABLE 5

Analysis results of cell contents, CMT and bacterial growth in cows Nos. 306, 331 and 333 from the first experiment round. Cows Nos. 306 and 331 were teat dipped on right rear and left forward teat, respectively, cow No. 333 was teat dipped on right forward and left rear teat, respectively.

| Cow # | exp. | | Day Time of | 23 am | pm | 24 am | pm | 25 am | pm | 26 am | pm | 27 am | pm | 28 am | pm | 29 am | pm |
|---|---|---|---|---|---|---|---|---|---|---|---|---|---|---|---|---|---|
| 306 | Cell | Hf | | 97 | 304 | 173 | 193 | 107 | 135 | 65 | 150 | 107 | 138 | 80 | 172 | 102 | 261 |
| | cont. | •Hb | | 158 | 331 | 208 | 221 | 237 | 303 | 128 | 179 | 193 | 245 | 124 | 143 | 108 | 220 |
| | | Vb | | 207 | 216 | 158 | 220 | 125 | 1659 | 28872 | 20590 | 16023 | 14595 | 9944 | 10211 | 3527 | 7958 |
| | | •Vf | | 1099 | 2133 | 764 | 2996 | 2008 | 2679 | 1052 | 2812 | 19707 | 14980 | 13471 | 13422 | 3839 | 6175 |
| | CMT | Hf | | 2 | 3 | 2 | 2 | 2 | 2 | 1 | 1 | 2 | 2 | 2 | 2 | 1 | 3 |
| | | •Hb | | 2 | 2 | 2 | 2 | 1 | 2 | 1 | 1 | 2 | 2 | 2 | 2 | 2 | 3 |
| | | Vb | | 1 | 2 | 1 | 2 | 2 | 4 | 5 | 5 | 5 | 5 | 5 | 5 | 4 | 5 |
| | | •Vf | | 3 | 3 | 3 | 4 | 4 | 4 | 3 | 5 | 5 | 5 | 5 | 5 | 4 | 4 |
| | Bact. | Hf | | | | | | | | | | | | | | | |
| | growth | •Hb | | | | | | | | | | | | | | | |
| | | Vb | | | | | | Sr | Sr | Sr | Sr | E Sr | E | | E | | |
| | | •Vf | | S | | S | S | Sr | Sr | Sr | Sr | Sr | Sr | | | | |
| 331 | Cell | Hf | | 72 | 126 | 53 | 101 | 60 | 93 | 62 | 128 | 84 | 111 | 63 | 99 | 31 | 102 |
| | cont. | •Hb | | 41 | 60 | 49 | 68 | 46 | 66 | 54 | 82 | 57 | 70 | 66 | 89 | 34 | 108 |
| | | Vb | | 30 | 42 | 26 | 45 | 45 | 56 | 66 | 114 | 194 | 159 | 126 | 194 | 12599 | 22497 |
| | | •Vf | | 46 | 57 | 42 | 74 | 48 | 67 | 44 | 126 | 47 | 82 | 50 | 91 | 38 | 84 |
| | CMT | Hf | | 1 | 2 | 1 | 2 | 1 | 2 | 1 | 1 | 2 | 1 | 1 | 2 | 1 | 2 |
| | | •Hb | | 1 | 1 | 1 | 2 | 1 | 1 | 1 | 1 | 1 | 1 | 1 | 1 | 1 | 2 |
| | | Vb | | 1 | 1 | 1 | 1 | 1 | 2 | 1 | 1 | 2 | 2 | 1 | 2 | 5 | 5 |
| | | •Vf | | 1 | 2 | 2 | 3 | 2 | 2 | 1 | 1 | 1 | 1 | 1 | 1 | 1 | 3 |
| | Bact. | Hf | | | | | | | | | | | | | | | |
| | growth | •Hb | | | | | | | | | | | | | | | |
| | | Vb | | | | | | | | | | | | Sr | Sr E | | Sr N |
| | | •Vf | | | | | | | | | | | | | | | |
| 333 | Cell | •Hf | | 92 | 387 | 173 | 198 | 120 | 131 | 131 | 169 | 81 | 108 | 86 | 152 | 45 | 96 |
| | cont | Hb | | 95 | 386 | 194 | 181 | 155 | 175 | 110 | 158 | 53 | 104 | 54 | 105 | 48 | 114 |
| | | •Vb | | 169 | 654 | 204 | 251 | 195 | 283 | 120 | 179 | 129 | 149 | 80 | 143 | 79 | 130 |
| | | Vf | | 113 | 739 | 255 | 267 | 156 | 252 | 138 | 297 | 80 | 142 | 85 | 131 | 59 | 92 |
| | CMT | •Hf | | 2 | 3 | 3 | 3 | 2 | 2 | 1 | 1 | 1 | 2 | 1 | 2 | 1 | 1 |
| | | Hb | | 1 | 3 | 3 | 3 | 3 | 2 | 1 | 1 | 1 | 2 | 1 | 2 | 1 | 1 |
| | | •Vb | | 2 | 3 | 3 | 3 | 3 | 2 | 1 | | 2 | 2 | 1 | 2 | 2 | 3 |
| | | Vf | | 1 | 3 | 3 | 3 | 2 | 2 | | 1 | 2 | 2 | 1 | 1 | 1 | 1 |
| | Bact. | •Hf | | | | | | | | | | | | | | | |
| | growth | Hb | | | | | | | | | | | | | | | |
| | | •Vb | | | | | | | | | | | | | | | |
| | | Vf | | | | | | | | | | | | | | | |

| Cow # | exp. | | Day Time of | 30 am | pm | 1 am | pm | 2 am | pm |
|---|---|---|---|---|---|---|---|---|---|
| 306 | Cell | Hf | | 119 | 205 | 88 | 192 | 36 | 100 |
| | cont. | •Hb | | 149 | 217 | 116 | 173 | 153 | 214 |
| | | Vb | | 2625 | 4080 | 1379 | 2941 | 1608 | 1692 |
| | | •Vf | | 2724 | 2793 | 1402 | 1957 | 935 | 1410 |
| | CMT | Hf | | 2 | 2 | 1 | 2 | 1 | 1 |
| | | •Hb | | 2 | 2 | 2 | 1 | 1 | 1 |
| | | Vb | | 3 | 4 | 3 | 2 | 2 | 2 |
| | | •Vf | | 3 | 4 | 3 | 1 | 1 | 2 |

TABLE 5-continued

Analysis results of cell contents, CMT and bacterial growth in cows Nos. 306, 331 and 333 from the first experiment round. Cows Nos. 306 and 331 were teat dipped on right rear and left forward teat, respectively, cow No. 333 was teat dipped on right forward and left rear teat, respectively.

|     |       |      |       |       |       |       |       |       |
|-----|-------|------|-------|-------|-------|-------|-------|-------|
|     | Bact. growth | Hf •Hb Vb •Vf |  |  |  |  |  | Sr |
| 331 | Cell cont. | Hf    | 102   | 118   | 85    | 118   | 50    | 77    |
|     |       | •Hb  | 136   | 246   | 139   | 166   | 58    | 64    |
|     |       | Vb   | 23828 | 32556 | 41565 | 25450 | 21898 | 13532 |
|     |       | •Vf  | 96    | 167   | 138   | 187   | 67    | 62    |
|     | CMT   | Hf   | 1     | 1     | 1     | 1     | 1     | 1     |
|     |       | •Hb  | 2     | 1     | 1     | 1     | 1     | 1     |
|     |       | Vb   | 5     | 5     | 5     | 5     | 5     | 5     |
|     |       | •Vf  | 2     | 2     | 1     | 1     | 1     | 1     |
|     | Bact. growth | Hf •Hb Vb •Vf |  |  |  |  |  |  |
|     |       | Vb   | Sr N  | Sr    | N Sr  | N Sr  | Sr    | E     |
| 333 | Cell cont. | •Hf | 78    | 96    | 48    | 78    | 69    | 125   |
|     |       | Hb   | 112   | 133   | 132   | 5099  | 39878 | 30290 |
|     |       | •Vb  | 255   | 160   | 122   | 242   | 165   | 305   |
|     |       | Vf   | 128   | 115   | 58    | 144   | 127   | 175   |
|     | CMT   | •Hf  | 1     | 1     | 1     | 1     | 1     | 1     |
|     |       | Hb   | 1     | 1     | 1     | 5     | 5     | 5     |
|     |       | •Vb  | 2     | 2     | 2     | 2     | 1     | 1     |
|     |       | Vf   | 2     | 1     | 1     | 1     | 1     | 1     |
|     | Bact. growth | •Hf |   |       |       |       |       |       |
|     |       | Hb   |       |       | Sr N  | Sr N  | Sr N  | Sr    |
|     |       | •Vb  |       |       |       |       |       |       |
|     |       | Vf   |       |       |       |       |       |       | am = morning
pm = afternoon
Hf = right forward teat
Hb = right rear teat
Vb = left rear teat
Vf = left forward teat
Cell cont = counted in 1000;
CMT = California Mastitis Test;
Bact. growth, Sr = *Streptococcus agalactiae*, S = Staphylococcus spp.;
E = Ethacilin;
• = teat-dipped;
N = Novocillin

TABLE 6

Analysis results of cell contents, CMT and bacterial growth in cow Nos. 334, 335 and 338 from the first experiment round. Cow Nos. 306 and 335 were teat dipped on right forward and left rear teat, respectively, cow No. 338 was teat dipped on right rear and left forward teat, respectively.

| Cow # | Day Time of exp. |     | 23 am | 23 pm | 24 am | 24 pm | 25 am | 25 pm | 26 am | 26 pm | 27 am | 27 pm | 28 am | 28 pm | 29 am | 29 pm |
|-------|------|------|------|------|------|------|------|------|------|------|------|------|------|------|------|------|
| 334 | Cell cont. | •Hf | 191 | 144 | 156 | 187 | 126 | 72 | 80 | 106 | 66 | 47 | 105 | 105 | 103 | 60 |
|     |            | Hb  | 83  | 87  | 97  | 98  | 63  | 65 | 56 | 78  | 80 | 73 | 67  | 106 | 81  | 108 |
|     |            | •Vb | 108 | 114 | 109 | 107 | 111 | 84 | 65 | 78  | 91 | 79 | 134 | 74  | 83  | 126 |
|     |            | Vf  | 117 | 164 | 130 | 143 | 16959 | 43705 | 44471 | 40411 | 35281 | 22651 | 23493 | 18960 | 16792 | 17835 |
|     | CMT        | •Hf | 1   | 2   | 2   | 2   | 1   | 1  | 1  | 1   | 1  | 1  | 2   | 2   | 2   | 1   |
|     |            | Hb  | 1   | 3   | 2   | 2   | 1   | 1  | 1  | 1   | 1  | 1  | 1   | 1   | 1   | 1   |
|     |            | •Vb | 1   | 3   | 2   | 2   | 1   | 1  | 1  | 1   | 2  | 1  | 1   | 1   | 1   | 1   |
|     |            | Vf  | 1   | 2   | 1   | 1   | 5   | 5  | 5  | 5   | 5  | 5  | 5   | 5   | 5   | 5   |
|     | Bact. growth | •Hf |   |   |   |   |   |   |   |   |   |   |   |   |   |   |
|     |              | Hb  |   |   |   |   |   |   | Sr |   |   |   |   |   |   |   |
|     |              | •Vb |   |   |   |   |   |   |   |   |   |   |   |   |   |   |
|     |              | Vf  |   |   |   |   | E | Sr | Sr E | Sr | Sr E | Sr |   |   |   |   |
| 335 | Cell cont  | •Hf | 87  | 86  | 64  | 83  | 318 | 1029 | 4187 | 4733 | 3369 | 2980 | 2289 | 2139 | 1032 | 1398 |
|     |            | Hb  | 100 | 101 | 58  | 96  | 14956 | 35956 | 45703 | 37195 | 32044 | 17631 | 9923 | 10081 | 6821 | 7330 |
|     |            | •Vb | 68  | 94  | 42  | 51  | 60  | 159 | 76 | 111 | 97 | 99 | 56 | 80 | 50 | 68 |
|     |            | Vf  | 80  | 75  | 38  | 67  | 688 | 1037 | 2204 | 2314 | 2061 | 2321 | 1353 | 2123 | 804 | 962 |
|     | CMT        | •Hf | 1   | 2   | 1   | 1   | 3   | 4  | 5  | 5   | 4  | 5  | 4   | 3   | 3   | 3   |
|     |            | Hb  | 1   | 1   | 1   | 1   | 5   | 5  | 5  | 5   | 5  | 5  | 5   | 5   | 5   | 4   |

TABLE 6-continued

Analysis results of cell contents, CMT and bacterial growth in cow Nos. 334, 335 and 338 from the first experiment round. Cow Nos. 306 and 335 were teat dipped on right forward and left rear teat, respectively, cow No. 338 was teat dipped on right rear and left forward teat, respectively.

|   |   |   |   |   |   |   |   |   |   |   |   |   |   |   |   |
|---|---|---|---|---|---|---|---|---|---|---|---|---|---|---|---|
|   |   | •Vb | 1 | 1 | 1 | 1 | 1 | 1 | 1 | 1 | 2 | 2 | 1 | 1 | 1 | 2 |
|   |   | Vf | 1 | 1 | 1 | 1 | 3 | 4 | 4 | 4 | 3 | 5 | 3 | 3 | 3 | 3 |
|   | Bact. | •Hf |   |   |   |   | Sr | Sr |   |   |   |   |   |   |   |   |
|   | growth | Hb |   |   |   |   | Sr E | Sr | Sr E | Sr | Sr | E |   |   |   |   |
|   |   | •Vb |   |   |   |   |   |   |   |   |   |   |   |   |   |   |
|   |   | Vf |   |   |   |   | Sr | Sr |   |   |   |   |   |   |   |   |
| 338 | Cell | Hf | 33 | 83 | 82 | 74 | 33 | 58 | 26 | 69 | 31 | 40 | 29 | 48 | 64 | 132 |
|   | cont. | •Hb | 193 | 130 | 77 | 118 | 49 | 65 | 21 | 74 | 97 | 73 | 43 | 80 | 68 | 99 |
|   |   | Vb | 146 | 90 | 69 | 146 | 112 | 150 | 62 | 130 | 49 | 105 | 44 | 98 | 133 | 121 |
|   |   | •Vf | 53 | 87 | 66 | 82 | 424 | 1685 | 2935 | 2005 | 1445 | 1348 | 650 | 994 | 395 | 392 |
|   | CMT | Hf | 1 | 1 | 1 | 1 | 1 | 1 | 1 | 1 | 1 | 1 | 1 | 1 | 1 | 3 |
|   |   | •Hb | 1 | 1 | 1 | 1 | 1 | 1 | 1 | 1 | 1 | 1 | 1 | 1 | 1 | 3 |
|   |   | Vb | 1 | 1 | 1 | 1 | 2 | 1 | 1 | 1 | 1 | 1 | 1 | 1 | 2 | 1 |
|   |   | •Vf | 1 | 1 | 1 | 1 | 3 | 4 | 4 | 4 | 3 | 3 | 2 | 3 | 2 | 2 |
|   | Bact. | Hf |   |   |   |   |   |   |   |   |   |   |   |   |   |   |
|   | growth | •Hb |   |   |   |   |   |   |   |   |   |   |   |   |   |   |
|   |   | Vb |   |   |   |   |   |   |   |   |   |   |   |   |   |   |
|   |   | •Vf | S |   |   |   | S | S |   |   |   |   |   |   |   |   |

| Cow # |   |   | Day Time of exp. | 30 am | pm | 1 am | pm | 2 am | pm |
|---|---|---|---|---|---|---|---|---|---|
| 334 | Cell | •Hf |   | 106 | 110 | 124 | 71 | 82 | 151 |
|   | cont. | Hb |   | 85 | 97 | 78 | 49 | 63 | 88 |
|   |   | •Vb |   | 106 | 73 | 81 | 105 | 65 | 75 |
|   |   | Vf |   | 8841 | 13602 | 4894 | 6013 | 1821 | 6099 |
|   | CMT | •Hf |   | 1 | 1 | 1 | 1 | 1 | 1 |
|   |   | Hb |   | 1 | 1 | 1 | 1 | 1 | 1 |
|   |   | •Vb |   | 1 | 1 | 1 | 1 | 1 | 1 |
|   |   | Vf |   | 5 | 5 | 4 | 3 | 3 | 3 |
|   | Bact. | •Hf |   |   |   |   |   |   |   |
|   | growth | Hb |   |   |   |   |   |   |   |
|   |   | •Vb |   | S |   |   |   |   |   |
|   |   | Vf |   |   |   |   |   |   |   |
| 335 | Cell | •Hf |   | 749 | 1325 | 675 | 964 | 483 | 10731 |
|   | cont | Hb |   | 4418 | 6865 | 3245 | 6150 | 2186 | 2855 |
|   |   | •Vb |   | 60 | 77 | 73 | 82 | 66 | 70 |
|   |   | Vf |   | 530 | 921 | 869 | 22227 | 19869 | 16789 |
|   | CMT | •Hf |   | 3 | 3 | 3 | 3 | 3 | 5 |
|   |   | Hb |   | 4 | 4 | 4 | 4 | 3 | 3 |
|   |   | •Vb |   | 1 | 1 | 1 | 2 | 1 | 1 |
|   |   | Vf |   | 3 | 3 | 3 | 5 | 5 | 5 |
|   | Bact. | •Hf |   |   |   |   |   | Sr | Sr (2) |
|   | growth | Hb |   |   |   |   |   |   | E |
|   |   | •Vb |   |   |   |   |   |   |   |
|   |   | Vf |   |   | Sr | Sr | Sr | Sr |   |
| 338 | Cell | Hf |   | 38 | 75 | 88 | 8862 | 30894 | 17377 |
|   | cont. | •Hb |   | 128 | 153 | 198 | 204 | 136 | 209 |
|   |   | Vb |   | 94 | 136 | 91 | 138 | 352 | 299 |
|   |   | •Vf |   | 257 | 501 | 387 | 692 | 566 | 621 |
|   | CMT | Hf |   | 1 | 1 | 1 | 5 | 5 | 5 |
|   |   | •Hb |   | 1 | 1 | 1 | 1 | 1 | 1 |
|   |   | Vb |   | 2 | 2 | 1 | 1 | 1 | 1 |
|   |   | •Vf |   | 3 | 2 | 3 | 2 | 2 | 3 |
|   | Bact. | Hf |   |   | Sr | Sr | Sr E | Sr |   |
|   | growth | •Hb |   |   |   |   |   |   |   |
|   |   | Vb |   |   | S |   |   |   |   |
|   |   | •Vf |   | S |   | S |   |   |   | am = morning
pm = afternoon
Hf = right forward teat
Hb = right rear teat
Vb = left rear teat
Vf = left forward teat
Cell cont = counted in 1000;
CMT = California Mastitis Test;
Bact. growth, Sr = *Streptococcus agalactiae*, S = Staphylococcus spp.;
E = Ethacilin;
• = teat-dipped;
N = Novocillin

TABLE 7

Analysis results of cell contents, CMT and bacterial growth in cow Nos. 306, 331, 334 and 338 from the second experiment round. Cow No. 306 was teat dipped on right forward teat, 331 was teat dipped on right forward and right rear teat, respectively, 334 and 338 were teat dipped on right rear teat.

| Cow # | | | Day<br>Time of<br>exp. | 13<br>am | pm | 14<br>am | pm | 15<br>am | pm | 16<br>am | pm | 17<br>am | pm | 18<br>am | pm | 19<br>am | pm |
|---|---|---|---|---|---|---|---|---|---|---|---|---|---|---|---|---|---|
| 306 | Cell | •Hf | | 89 | 160 | 141 | 235 | 91 | 131 | 129 | 143 | 108 | 95 | | | | |
| | cont. | Hb | | 78 | 131 | 127 | 123 | 31822 | 38666 | 39981 | 16350 | 19969 | 12399 | | | | |
| | CMT | •Hf | | 2 | 3 | 2 | 3 | 2 | 2 | 2 | 2 | 2 | 2 | | | | |
| | | Hb | | 2 | 3 | 1 | 2 | 3 | 5 | 5 | 5 | 5 | 5 | | | | |
| | Bact. | •Hf | | | | | | | | | | | | | | | |
| | growth | Hb | | | | | E | Sr | Sr E | Sr | | E | | E | | E | |
| 331 | Cell | •Hf | | 58 | 112 | 76 | 72 | 69 | 97 | 46 | 88 | 56 | 95 | 62 | 96 | 148 | 6 |
| | cont | •Hb | | 75 | 109 | 92 | 74 | 73 | 75 | 69 | 1011 | 68 | 133 | 133 | 130 | 211 | 174 |
| | | Vf | | 50 | 67 | 65 | 55 | 51 | 39 | 33 | 48 | 41 | 50 | 375 | 26511 | 44130 | 35022 |
| | CMT | •Hf | | 1 | 3 | 1 | 1 | 2 | 2 | 1 | 1 | 2 | 2 | 2 | 1 | 2 | 1 |
| | | •Hb | | 2 | 2 | 1 | 1 | 3 | 2 | 1 | 1 | 2 | 2 | 1 | 2 | 2 | 3 |
| | | Vf | | 1 | 1 | 1 | 2 | 1 | 1 | 1 | 1 | 1 | 1 | 4 | 5 | 5 | 5 |
| | Bact. | •Hf | | | | | | | | | | | | | | | |
| | growth | •Hb | | | | | | | | | | | | | | | |
| | | Vf | | | | | | | | | | | | Sr E | Sr | Sr E | Sr |
| 334 | Cell | Hf | | 116 | 149 | 113 | 159 | 108 | 143 | 144 | 174 | 112 | | | | | |
| | cont | •Hb | | 47 | 62 | 56 | 71 | 6870 | 26446 | 43123 | 36795 | 27753 | | | | | |
| | | Vb | | 47 | 62 | 86 | 333 | 2686 | 2550 | 1459 | 1561 | 1816 | | | | | |
| | CMT | Hf | | 1 | 1 | 1 | 2 | 2 | 3 | 1 | 1 | 1 | | | | | |
| | | •Hb | | 1 | 1 | 1 | 1 | 4 | 5 | 5 | 5 | 5 | | | | | |
| | | Vb | | 1 | 1 | 1 | 3 | 3 | 3 | 3 | 3 | 3 | | | | | |
| | Bact. | Hf | | | | | | Sr | Sr | | | | | | | | |
| | growth | •Hb | | | | | E | Sr | Sr E | Sr | Sr | E | | E | | E | |
| | | Vb | | | | | | S | Sr | | | | | | | | |
| 338 | Cell | •Hb | | 50 | 135 | 29 | 64 | 44 | 56 | 28 | 34 | 33 | 47 | 39 | 56 | 110 | 145 |
| | cont. | Vb | | 32 | 88 | 26 | 35 | 26 | 57 | 18 | 43 | 21 | 47 | 35 | 9548 | 29784 | 25099 |
| | CMT | •Hb | | 1 | 1 | 1 | 1 | 1 | 1 | 1 | 1 | 1 | 1 | 1 | 1 | 3 | 3 |
| | | Vb | | 1 | 1 | 1 | 1 | 1 | 1 | 1 | 1 | 1 | 1 | 1 | 5 | 5 | 5 |
| | Bact. | •Hb | | | | | | | | | | | | | | | |
| | growth | Vb | | | | | | | | | | | | Sr E | Sr | Sr E | Sr | am = morning
pm = afternoon
Hf = right forward teat
Hb = right rear teat
Vb = left rear teat
Vf = left forward teat
Cell cont = counted in 1000;
CMT = California Mastitis Test;
Bact. growth, Sr = *Streptococcus agalactiae*;
S = Staphylococcus spp.;
E = Ethacilin;
• = teat-dipped;
N = Novocillin

TABLE 8

Analysis results of cell contents, CMT and bacterial growth in cow Nos. 306, 331, 333 and 335 from the third experiment round with commercial teat dipping composition. Cow No. 306 was teat dipped on right forward teat, cow No. 331 on right forward and right rear teat, respectively, cow No. 333 on right forward, left rear teat and left forward teat, respectively, and cow No. 335 on left rear teat.

| Cow # | | | Day<br>Time of<br>exp. | 28<br>am | pm | 29<br>am | pm | 30<br>am | pm | 31<br>am | pm | 1<br>am | pm | 2<br>pm | 3<br>am | pm | 4<br>am | pm | am |
|---|---|---|---|---|---|---|---|---|---|---|---|---|---|---|---|---|---|---|---|
| 306 | Cell<br>cont. | Hf | | 96 | 144 | 107 | 155 | 57 | 132 | 114 | 114 | 125 | 152 | 62 | 66 | 129 | 89 | 115 | 104 |
| | CMT | Hf | | 1 | 1 | 1 | 1 | 1 | 1 | 1 | 1 | 1 | 1 | 1 | 1 | 2 | 1 | 2 | 2 |
| | Bact.<br>growth | Hf | | | | | | | | | | | | | | | | | Sr |

TABLE 8-continued

Analysis results of cell contents, CMT and bacterial growth in cow Nos. 306, 331, 333 and 335 from the third experiment round with commercial teat dipping composition. Cow No. 306 was teat dipped on right forward teat, cow No. 331 on right forward and right rear teat, respectively, cow No. 333 on right forward, left rear teat and left forward teat, respectively, and cow No. 335 on left rear teat.

| | | | | | | | | | | | | | | | | | | |
|---|---|---|---|---|---|---|---|---|---|---|---|---|---|---|---|---|---|---|
| 331 | Cell cont | Hf | 42 | 64 | 82 | 153 | 59 | 125 | 58 | 86 | 53 | 158 | 72 | 88 | 248 | 129 | 224 | 121 |
| | | Hb | 51 | 67 | 86 | 109 | 86 | 113 | 74 | 91 | 66 | 107 | 100 | 61 | 114 | 101 | 143 | 107 |
| | CMT | Hf | 2 | 1 | 1 | 1 | 1 | 1 | 1 | 2 | 1 | 1 | 1 | 2 | 2 | 2 | 2 | 2 |
| | | Hb | 2 | 1 | 1 | 1 | 1 | 2 | 1 | 2 | 1 | 1 | 1 | 2 | 2 | 2 | 3 | 2 |
| | Bact. growth | Hf Hb | | | | | | | | | | | | | | | | |
| 333 | Cell cont | Hf | 49 | 95 | 34 | 104 | 44 | 139 | 103 | 159 | 107 | 199 | 250 | 93 | 217 | 134 | 207 | 192 |
| | | Vb | 73 | 150 | 85 | 131 | 73 | 115 | 91 | 114 | 44 | 83 | 83 | 72 | 135 | 141 | 208 | 164 |
| | | Vf | 81 | 133 | 82 | 195 | 68 | 195 | 119 | 156 | 106 | 184 | 167 | 146 | 263 | 172 | 278 | 198 |
| | CMT | Hf | 1 | 2 | 1 | 1 | 1 | 3 | 2 | 3 | 1 | 2 | 2 | 2 | 2 | 3 | 3 | 2 |
| | | Vb | 2 | 2 | 3 | 1 | 3 | 2 | 1 | 3 | 1 | 2 | 2 | 2 | 2 | 3 | 3 | 2 |
| | | Vf | 3 | 2 | 1 | 1 | 3 | 3 | 2 | 3 | 2 | 3 | 2 | 2 | 3 | 3 | 1 | 2 |
| | Bact. growth | Hf Vb Vf | | | | | | | | | | | | | | | | |
| 335 | Cell cont. | Vb | 115 | 133 | 118 | 144 | 106 | 144 | 225 | 333 | 265 | 456 | 316 | 434 | 605 | 251 | 280 | 240 |
| | CMT | Vb | 3 | 2 | 3 | 1 | 3 | 3 | 2 | 3 | 2 | 3 | 2 | 2 | 3 | 3 | 1 | 2 |
| | Bact. growth | Vb | | | | | | | | | | | | | | | | Sr |

| | | | Day | 5 | | 6 | |
|---|---|---|---|---|---|---|---|
| Cow # | | | Time of exp. | pm | am | pm | |
| 306 | Cell cont. | Hf | | 12055 | 38455 | | |
| | CMT | Hf | | 5 | 5 | | |
| | Bact. growth | Hf | | Sr | Sr | | |
| 331 | Cell cont | Hf | | 208 | 148 | 271 | 143 |
| | | Hb | | 187 | 114 | 136 | 118 |
| | CMT | Hf | | 1 | 2 | 3 | |
| | | Hb | | 2 | 2 | 2 | |
| | Bact. growth | Hf Hb | | | | | |
| 333 | Cell cont | Hf | | 258 | 179 | 326 | 195 |
| | | Vb | | 288 | 118 | 147 | 81 |
| | | Vf | | 278 | 137 | 237 | 94 |
| | CMT | Hf | | 3 | 2 | 3 | |
| | | Vb | | 2 | 2 | 2 | |
| | | Vf | | 2 | 2 | 2 | |
| | Bact. growth | Hf Vb Vf | | | | | |
| 335 | Cell cont. | Vb | | 7997 | 23298 | | |
| | CMT | Vb | | 5 | 5 | | |
| | Bact. growth | Vb | | Sr | Sr | | | am = morning
pm = afternoon
Hf = right forward teat
Hb = right rear teat
Vb = left rear teat
Vf = left forward teat
Cell cont = counted in 1000;
CMT = California Mastitis Test;
Bact. growth, Sr = *Streptococcus agalactiae*, S = Staphylococcus spp.;
E = Ethacilin;

What is claimed is:

1. A method for the prophylactic treatment of a lactating animal against mastitis comprising applying to the teats of a lactating animal in need of said prophylactic treatment a composition comprising:
   chitosan,
   a polysaccharide selected from the group consisting of heparin and dextran sulfate, and
   a solvent;
   wherein the total concentration of chitosan and polysaccharide in said composition is within a range of 0.2–10 percent by weight, based on the weight of said composition; wherein the composition is in the form of a solution; and wherein the weight ratio of chitosan:polysaccharide is within the range of 100:1–10:1.

2. The method of claim 1, wherein said lactating animal is a cow.

3. The method of claim 1, wherein said chitosan has a degree of N-acetylation of at most about 90%.

4. The method of claim 3, wherein said degree of N-acetylation is at most about 50%.

5. The method of claim 4, wherein said degree of N-acetylation is at most about 25%.

6. The method of claim 1, wherein said polysaccharide is heparin.

7. The method of claim 1, wherein said polysaccharide is dextran sulfate.

8. The method of claim 1, wherein said solvent is water based.

9. The method of claim 8, wherein said solvent is water.

10. The method of claim 1, wherein said total concentration of chitosan and polysaccharide is within the range of 0.2–5 percent by weight, based on the weight of said composition.

11. The method of claim 10, wherein said total concentration of chitosan and polysaccharide is within the range of 0.25–3 percent by weight, based on the weight of said composition.

12. The method of claim 1, wherein said weight ratio is within the range of 60:1–15:1.

13. The method of claim 1, wherein said chitosan and polysaccharide are present in said composition in amounts that result in a bacterial barrier or bacteriostatic effect when said composition is applied.

14. The method of claim 1, wherein said chitosan and polysaccharide are present in said composition in amounts that result in a wound healing effect when said composition is applied.

15. The method of claim 1, wherein said chitosan and polysaccharide are present in said composition in amounts that result in a therapeutic effect against mastitis when said composition is applied.

16. The method of claim 1, wherein said composition further comprises a viscosity controlling agent.

17. The method of claim 16, wherein said viscosity controlling agent is a cellulose derivative or glycerol.

18. The method of claim 17, wherein said cellulose derivative is selected from the group consisting of methyl cellulose, ethyl cellulose, hydroxyethylcellulose and carboxymethyl cellulose.

19. The method of claim 17, wherein the viscosity controlling agent is glycerol.

20. The method of claim 1, wherein said composition is applied to the teats of said lactating animal by dipping or spraying.

21. The method of claim 1, wherein the composition prophylactically treats mastitis caused by a bacterial infection.

* * * * *